US011191761B2

(12) United States Patent
Guo et al.

(10) Patent No.: US 11,191,761 B2
(45) Date of Patent: Dec. 7, 2021

(54) SOMCL-9112 SOLID DISPERSION AND PREPARATION METHOD THEREOF AND SOMCL-9112 SOLID PREPARATION CONTAINING SOMCL-9112 SOLID DISPERSION

(71) Applicants: SHANGHAI INSTITUTE OF MATERIA MEDICA, CHINESE ACADEMY OF SCIENCES, Shanghai (CN); Shanghai Acebright Pharmaceuticals Co., Ltd., Pudong New District Shanghai (CN)

(72) Inventors: Shiyan Guo, Shanghai (CN); Yong Gan, Shanghai (CN); Ao Zhang, Shanghai (CN); Zehong Miao, Shanghai (CN); Li Gao, Shanghai (CN); Jian Ding, Shanghai (CN)

(73) Assignees: SHANGHAI INSTITUTE OF MATERIA MEDICA, CHINESE ACADEMY OF SCIENCES, Shanghai (CN); SHANGHAI ACEBRIGHT PHARMACEUTICALS CO., LTD., Shanghai (CN)

(*) Notice: Subject to any disclaimer, the term of this patent is extended or adjusted under 35 U.S.C. 154(b) by 0 days.

(21) Appl. No.: 15/574,557

(22) PCT Filed: May 13, 2016

(86) PCT No.: PCT/CN2016/082044
§ 371 (c)(1),
(2) Date: Nov. 16, 2017

(87) PCT Pub. No.: WO2016/184367
PCT Pub. Date: Nov. 24, 2016

(65) Prior Publication Data
US 2018/0133215 A1 May 17, 2018

(30) Foreign Application Priority Data
May 18, 2015 (CN) .......................... 201510253480.7

(51) Int. Cl.
| | | |
|---|---|---|
| A61K 31/502 | (2006.01) | |
| A61K 47/40 | (2006.01) | |
| A61K 47/38 | (2006.01) | |
| A61K 47/34 | (2017.01) | |
| A61K 47/32 | (2006.01) | |
| A61K 9/48 | (2006.01) | |
| A61K 9/28 | (2006.01) | |
| A61P 35/00 | (2006.01) | |
| A61K 47/10 | (2017.01) | |
| A61K 9/10 | (2006.01) | |
| A61K 9/20 | (2006.01) | |
| A61K 9/08 | (2006.01) | |
| A61K 9/14 | (2006.01) | |

(52) U.S. Cl.
CPC .............. *A61K 31/502* (2013.01); *A61K 9/08* (2013.01); *A61K 9/10* (2013.01); *A61K 9/146* (2013.01); *A61K 9/2018* (2013.01); *A61K 9/2054* (2013.01); *A61K 9/28* (2013.01); *A61K 9/4858* (2013.01); *A61K 9/4866* (2013.01); *A61K 47/10* (2013.01); *A61K 47/32* (2013.01); *A61K 47/34* (2013.01); *A61K 47/38* (2013.01); *A61K 47/40* (2013.01); *A61P 35/00* (2018.01)

(58) Field of Classification Search
CPC .......... A61K 31/502; A61K 9/10; A61K 9/28; A61P 35/00
See application file for complete search history.

(56) References Cited

U.S. PATENT DOCUMENTS

| | | | | |
|---|---|---|---|---|
| 8,475,842 | B2 * | 7/2013 | Bechtold | .............. A61K 9/2027 |
| | | | | 424/486 |
| 2015/0011525 | A1 * | 1/2015 | Bi | .......................... A61K 9/146 |
| | | | | 514/210.02 |
| 2015/0166544 | A1 * | 6/2015 | Zhang | .................. C07D 487/04 |
| | | | | 514/249 |

FOREIGN PATENT DOCUMENTS

| | | | | |
|---|---|---|---|---|
| CN | 102238945 A | | 11/2011 | |
| CN | 103833756 A | | 6/2014 | |
| CN | WO2014/019468 | * | 6/2014 | |
| WO | 2014019468 A1 | | 2/2014 | |
| WO | WO-2014019468 A1 | * | 2/2014 | ........... C07D 487/04 |
| WO | 2014205105 A1 | | 12/2014 | |

OTHER PUBLICATIONS

Senra et al. In Molecular Cancer Therapeutics 10(10), 1949-1958 (2011) (Year: 2011).*
Savjani et al. In ISRN Pharmaceutics Article ID 195727 (2012) (Year: 2012).*

(Continued)

*Primary Examiner* — Dennis Heyer
(74) *Attorney, Agent, or Firm* — Panitch Schwarze Belisario & Nadel LLP; Lars H. Genieser (57) ABSTRACT

Disclosed is an SOMCL-9112 solid dispersion. The SOMCL-9112 solid dispersion is characterized by being prepared from the following raw materials in percentage by weight: 5 percent to 60 percent of SOMCL-9112, 5 percent to 90 percent of pharmaceutically acceptable matrix polymer, 0 percent to 20 percent of surfactant, 0 percent to 20 percent of flow aid and 0 percent to 20 percent of plasticizer. Also disclosed are a preparation method of the SOMCL-9112 solid dispersion, a solid medicinal preparation containing the solid dispersion and application of the solid dispersion for preparing a medicine for treating cancer.

28 Claims, 3 Drawing Sheets

(56) References Cited

OTHER PUBLICATIONS

Lynparza at https://www.lynparza.com/what-is-lynparza.html (retireved from the internt Jul. 26, 2021) (Year: 2021).*
Javle et al. JAMA Oncology 7(5), 693-699 (2021) (Year: 2021).*
Int'l Search Report dated Aug. 17, 2016 in Int'l Application No. PCT/CN2016/082044.
Zhang, et al., "Research Progress on Excipients of Solid Dispersion Prepared by Hot-Melt Extrusion Technique", Drugs & Clinic, vol. 29, No. 5, pp. 557-563 (2014); English Abstract only.
Hashida, Mitsuru, "Design and evaluation of formulation for oral administration," Pharmaceutical Affairs Timetable, pp. 172-184 (Feb. 1995).
Office Action dated Dec. 11, 2018 in JP Application No. 2018512468 (Partial English Translation).

* cited by examiner

SOMCL-9112 SOLID DISPERSION AND PREPARATION METHOD THEREOF AND SOMCL-9112 SOLID PREPARATION CONTAINING SOMCL-9112 SOLID DISPERSION

CROSS-REFERENCE TO RELATED APPLICATION

This application is a Section 371 of International Application No. PCT/CN2016/082044, filed May 13, 2016, which was published in the Chinese language on Nov. 24, 2016, under International Publication No. WO 2016/184367 A1, which claims priority to Chinese Patent Application No. 2015102534807, filed May 18, 2015. Each disclosure is incorporated herein by reference in its entirety.

TECHNICAL FIELD

The present invention relates to the field of pharmaceutical preparations and relates to a SOMCL-9112 solid dispersion, a preparation method thereof and a solid pharmaceutical preparation comprising said solid dispersion and use of said solid dispersion for the preparation of a medicament for the treatment of cancer.

BACKGROUND ART

SOMCL-9112, chemical name of which is 4-(4-fluoro-3-(5-methyl-3-(trifluoromethyl)-5,6,7,8-4H-[1,2,4]triazolo[4,3-a]piperazine-7-carbonyl)benzyl)phthalazin-1(2H)-one, molecular formula of which is $C_{23}H_{18}F_4N_6O_2$, and molecular weight of which is 486.4, has the following chemical structure:

In CN103833756A and PCT/CN2013/079998, SOMCL-9112 and use thereof have been disclosed and listed. In the earlier researches, SOMCL-9112, as a novel polyadenosine diphosphate ribose polymerase-1 (PARP1) inhibitor with high selectivity, was used for the treatment of the PARP-related diseases, especially for the treatment of cancer, such as breast cancer, pancreatic cancer, ovarian cancer and the like.

SOMCL-9112 is particularly effective in treating cancer cells in which are defective in homologous recombinant (HR)-dependent DNA double-strand break (DSB) repair pathway. BRCA1 (NM_007295) and BRCA2 (NM_000059) hereditary breast cancer/ovarian cancer genes are only two among many proteins in HR-dependent DNA DSB repair pathway. Compared with cancers with no defects in homologous recombinant (HR)-dependent DNA double-strand break (DSB) repair pathway, the $brca1^{-/-}$ and/or $brca2^{-/-}$ can be better treated by PARP inhibitors, which may achieve effective monotherapy and/or combination therapy.

The equilibrium solubility of SOMCL-9112 in pH 1.2-6.8 buffer saline solution is below 0.10 mg/ml and it is a water insoluble drug. When Caco-2 cell line was studied, the permeation coefficient of SOMCL-9112 was comparable to that of atenolol, a low permeability positive control, and Caco-2 Papp value was $0.72\times10^{-6}$ cm/s (see Experiment Example 1). According to the measurement results of solubility and penetration of drugs, it can be predicted that in vivo adsorption of SOMCL-9112 is poor and bioavailability is low. The bioavailability of oral administration of SOMCL-9112 by a patient depends on the dissolution rate and solubility of the drug in the GI intestine to a certain extent. The bioavailability of SOMCL-9112 in different formulation forms after administration can be assessed by measuring the concentration of SOMCL-9112 in the plasma and calculating the area under the drug-time curve. In the rat PK test, the in vivo exposure amount of SOMCL-9112 nano-crystalline preparation was extremely low (see Experiment Example 2), and the area under the drug-time curve after 24 hours of administration was only 126 h*ng/ml, so as to affect the normal efficacy of the drug. So the studies were conducted to improve the bioavailability of SOMCL-9112.

At present, prodrug modification and salification of insoluble drugs have been widely used to improve its solubility and bioavailability. However, the above methods have some limitations, such as complex operation, many intermediate products and high cost and it is difficult to achieve large-scale industrial production. In 1961, Sekiguchi et al. firstly applied solid dispersion technology to improve the solubility and bioavailability of insoluble drugs. Many pharmaceutical researchers have conducted extensive and deep studies on solid dispersions and further demonstrated that preparing insoluble drugs into solid dispersions is one of the methods with profound development potential to improve solubility and bioavailability. The pharmaceutical preparations prepared by solid dispersion technology have been commercialized, such as Kaletra (lopinavir/ritonavir).

SUMMARY OF THE INVENTION

In the present invention, a SOMCL-9112 pharmaceutical formulation with high bioavailability has been developed to meet the needs of clinical administration under the premise of achieving adequate drug loading and stability. In the present invention, the SOMCL-9112 solid dispersion can form stable mixed micelles with an average particle size of ~100 nm in a simulated gastrointestinal fluid, and the solubility of SOMCL-9112 can be increased from ~10 μg/ml to more than 300 μg/ml. The drug solubility is improved and the drug precipitation is prevented by the micelle solubilization principle thereby improving the bioavailability of drugs. The increased bioavailability facilitates to reduce dose required to achieve a considerable exposure amount of SOMCL-9112 observed when the conventional formulation is used and can reduces the effective therapeutic dose, improves drug efficacy, saves drug cost and reduces the side effects of the drug.

In the first aspect of the present invention, a SOMCL-9112 solid dispersion is provided, which comprises following raw materials,

| | |
|---|---|
| SOMCL-9112 | 5%-60%, preferably 10%-50% |
| a pharmaceutically acceptable matrix polymer | 5%-90%, preferably 10%-80% |
| a surfactant | 0%-20%, preferably 0.5%-15% |
| a glidant | 0%-20%, preferably 0%-15% |
| a plasticizer | 0%-20%, preferably 0%-10%. |

In the SOMCL-9112 solid dispersion provided in the present invention, the proportion of SOMCL-9112 present in an amorphous form in SOMCL-9112 ranges from 70% to 100%, preferably 80% or more, more preferably 90% or more, and further preferably 95% or more, and most preferably, all SOMCL-9112 is substantially present in an amorphous form. SOMCL-9112 in the SOMCL-9112 solid dispersion can be stabilized in amorphous form and the possibility of conversion or reversal of SOMCL-9112 into other forms can be reduced. The SOMCL-9112 solid dispersion provided in the present invention can overcome shortcomings of poor physical stability and easy aging of the conventional solid dispersion. In one example of the present invention, the solid dispersion prepared from SOMCL-9112 and a pharmaceutically acceptable matrix polymer is still stable amorphous form after 6 months of loading under accelerated conditions and has good stability.

The pharmaceutically acceptable matrix polymer has a Tg of at least about 50° C. and may be one or more selected from a group consisting of copovidone, povidone, hydroxypropylmethylcellulose phthalate (HPMPCP), hydroxypropylmethylcellulose acetate succinate (HPMCAS), 2-hydroxy-β-cyclodextrin (HPBCD), hydroxypropylmethylcellulose (HPMC), polymethacrylate, polyvinyl caprolactam-polyvinyl acetate-polyethylene glycol graft copolymer (Soluplus), hydroxypropylcellulose (HPC) and cellulose acetate phthalate (CAP), preferably one or more from a group consisting of copovidone, Soluplus and hydroxypropylmethylcellulose acetate succinate. Copovidone is a water-soluble organic high molecular compound and is a linear copolymer of N-vinylpyrrolidone (NVP) and vinyl acetate (VA). Wherein, the VA content is nominally about 40% (but may be different, e.g., 35 to 41%). The average molecular weight (Mw) is from 24 000 to 30 000.

More preferably, the weight ratio of SOMCL-9112 to the pharmaceutically acceptable matrix polymer is from 1:0.25 to 1:10, preferably from 1:0.3 to 1:7, more preferably from 1:0.5 to 1:5, and more preferably from 1:2 to 1:4.

In the present invention, the surfactant can further enhance the improvement of the therapeutic potential of the solid dispersion of the present invention. Suitable surfactant includes: anionic surfactant such as sodium dodecyl sulfate (sodium lauryl sulfate) and docusate sodium; cationic surfactant such as bromo-trimethylammonium, benzethonium chloride, cetylpyridinium chloride and lauric acid; and non-ionic surfactant such as polyoxyethylene alkyl ether, polyoxyethylene sorbitan fatty acid ester (specifically, such as Tween 80, 60, 40 and 20), polyoxyethylene castor oil derivative (specifically, Cremophor RH40), polyoxyethylene stearate and poloxamer; preferably sodium dodecyl sulfate.

The glidant is one or more selected from a group consisting of colloidal silica, animal or vegetable fat, wax and the like.

The presence of the plasticizer can improve the workability of the solid dispersion. The suitable plasticizer is one or more selected from a group consisting of acetyl tributyl citrate, acetyl triethyl citrate, benzyl benzoate, chlorobutanol, dextrin, dibutyl phthalate, diethyl phthalate, dimethyl phthalate, glycerol, glyceryl monostearate, mannitol, mineral oil, lanolin alcohol, palmitic acid, polyethylene glycol, polyvinyl acetate phthalate, propylene glycol, 2-pyrrolidone, sorbitol, stearic acid, triacetin, tributyl citrate, triethanolamine and triethyl citrate.

The solid dispersion of the present invention may also contain other additives, if necessary such as lubricant, filler, disintegrant, stabilizer (e.g., antioxidant, light stabilizer, radical scavenger, stabilizer against microbial attack, etc.) and the like. The specific selection range and amount of the other additives are conventional options for those skilled in the art.

The disintegrant promotes rapid disintegration of the solid preparation in the stomach and keeps the released particles separated from each other. Suitable disintegrant includes cross-linked polymer such as croscarmellose sodium, cross-linked polyvinylpyrrolidone (i.e., crospovidone PVPP).

The suitable filler is one or more selected from a group consisting of lactose, sucrose, mannitol, calcium hydrogen phosphate, microcrystalline cellulose, starch, isomaltose and the like.

The suitable lubricant is one or more selected from a group consisting of polyethylene glycol (e.g., molecular weight of 1000 to 6000), magnesium stearate, calcium stearate, sodium stearyl fumarate, and the like.

The SOMCL-9112 solid dispersion provided in the present invention can form stable mixed micelles with an average particle size of ~100 nm in a simulated gastrointestinal fluid, and the solubility of SOMCL-9112 can be increased from ~10 μg/ml to more than 300 μg/ml. Compared with ordinary solid dispersions, the formed mixed micelles can overcome shortcomings of ordinary solid dispersion drug which is easy to precipitate by increasing the drug solubility while avoiding drug precipitation through micellar solubilization principle. The solid dispersion provided by the present invention can improve the bioavailability of the drug by increasing the drug solubility and preventing the drug from precipitating.

In another aspect of the present invention, a process for the preparation of the above SOMCL-9112 solid dispersion is provided, comprising steps of:

(1) uniformly mixing raw materials by melting or dissolving to obtain a homogeneous dispersion;

(2) solidifying the homogeneous dispersion to give SOMCL-9112 solid dispersion wherein SOMCL-9112 is present in an amorphous form.

The above SOMCL-9112 solid dispersion may be prepared by a solvent evaporation method or a melt extrusion method, preferably a melt extrusion method.

The melt extrusion process produces a melt by applying heat and/or mechanical stress, "melt" refers to a liquid state or a rubbery state, where a component may be uniformly embedded in the other components. In general, one component melts and other components are dissolved in the melted component to form a melt. The formation of the melt generally involves the softening point of the pharmaceutically acceptable matrix polymer, and the melt can be prepared by a variety of methods. The components may be mixed before, during or after the formation of the melt. For example, the components are mixed followed by being heated or simultaneously mixed and heated. In general, active materials in the melt should be uniformly dispersed and the melt is pasty or viscous. Typically, the heating temperature is from 70° C. to 250° C., preferably from 80° C. to 200° C., and most preferably from 100° C. to 180° C.

The production and extrusion of the melt in steps (1) and (2) in the melt extrusion process can be carried out in a conventional apparatus for this purpose. The extruder and kneader are particularly suitable. The suitable extruder may be a screw extruder, including a single screw extruder, double screw extruder or other multi screw extruder, preferably a double screw extruder, which may rotate clockwise or reversely, and optionally equipped with a kneading plate. It will be appreciated that the operating temperature will also be determined by the type of extruder or the type of construction of the used extruder. The part of the energy required to melt, mix and dissolve the components in the extruder can be provided by means of heating elements. The friction and shear of the material in the extruder can also provide a significant amount of energy to the mixture to help the formation of uniform melt. The extrudate can be obtained using a molding module of an extruder and can be cut into pieces before or after curing.

In one embodiment, the preparation method for the SOMCL-9112 solid dispersion comprises steps of:

(1a) mixing raw materials and heating to produce a melt;
(2a) extruding the melt to cure for producing a SOMCL-9112 solid dispersion.

The heating temperature in step (1a) is 70° C.-250° C., preferably 80° C.-200° C., and most preferably 100° C.-180° C.

In another embodiment, the preparation method for the SOMCL-9112 solid dispersion comprises steps of:

(1b) dissolving raw materials in a solvent;
(2b) evaporating the solvent to produce a SOMCL-9112 solid dispersion wherein SOMCL-9112 is present in an amorphous form.

In step (1b), the suitable solvent may be selected according to the pharmaceutically acceptable matrix polymer and be selected from a group consisting of acetone, acetone/dichloromethane, methanol/dichloromethane, acetone/water, acetone/methanol, acetone/ethanol, dichloromethane/ethanol or ethanol/water, etc., wherein "/" represents a mixed solvent of both.

The method for evaporating the solvent in step (2b) comprises rotary evaporation, spray drying, lyophilization and thin film evaporation. Alternatively, the solvent may be removed by freezing at low temperature followed by lyophilization. Other techniques such as melt extrusion, solvent controlled precipitation, pH controlled precipitation and low temperature co-grinding may also be used.

In yet another aspect of the present invention, a SOMCL-9112 solid preparation is provided, which comprises the SOMCL-9112 solid dispersion and a non-essential pharmaceutical additive.

The pharmaceutical additive may be one or more selected from a group consisting of a glidant, a disintegrant, a filler, a lubricant, a coating agent and the like.

The descriptions of the glidant, disintegrant, filler and lubricant are the same as described above.

The film coating improves taste and provides a delicate look. If desired, the film coating may be an enteric coating. The film coating typically comprises polymeric film-forming material such as hydroxypropylmethylcellulose, hydroxypropylcellulose and acrylate or methacrylate copolymers. In addition to the film-forming polymer, the film coating may also contain plasticizer such as polyethylene glycol, surfactant such as Tween, and optional pigment such as titanium dioxide or iron oxides. The film coating may also contain talc as an anti-tack agent. Such additives may comprise from about 0 to about 20% by weight of the total solids. The film coating of a tablet also helps to swallow comfortably.

In the present invention, a method for preparing the SOMCL-9112 solid preparation is also provided, comprising the following step: treating the SOMCL-9112 solid dispersion and mixing the same with a pharmaceutically acceptable additive to prepare a formulation.

The "treating" means that the SOMCL-9112 solid dispersion is made into a powder or granule suitable for making the formulation, including, for example, pulverization, milling or grinding.

The SOMCL-9112 solid formulation may comprise from 2 to 1500 mg of SOMCL-9112. The patient may be an adult or a child, but also be other mammals to be treated. In one example of these aspects, the used pharmaceutically acceptable matrix polymer is copovidone and the SOMCL-9112 solid formulation of the present invention has a higher bioavailability compared with formulations obtained in other ways (in one example of these respects, the relative bioavailability of the SOMCL-9112 solid formulation was 724.6% of that of the nanocrystalline suspension (Experiment Example 2) and the absolute bioavailability of the SOMCL-9112 solid formulation was 40.2% (Experiment Example 3)). The increased bioavailability facilitates to reduce dose required to achieve a considerable exposure amount of SOMCL-9112 observed when the conventional formulation such as SOMCL-9112 IR tablet is used and can reduce the effective therapeutic dose, improve drug efficacy, save drug cost and reduce the side effects of the drug.

The SOMCL-9112 solid preparation provided by the present invention is a preparation suitable for mucosal administration to a patient and can be administered to a mucosa for absorption through the membrane. To this end, the suitable routes of administration include administration by inhalation, as well as oral, intranasal and rectal administration. Particularly preferred is oral administration. The skilled person may select a tablet, capsule or other formulation depending on the route of administration. However, other routes of administration are not excluded, such as extra-intestine.

For example, the SOMCL-9112 solid preparation according to the present invention may be tablet, capsule, granule, powder and the like.

Use of the solid dispersion of SOMCL-9112 in the manufacture of a medicament for the treatment of cancer is also provided in the present invention.

SOMCL-9112 has a significant inhibitory effect on poly-ADP-ribose polymerase (PARP), which can be used to prepare drugs for the treatment of cancer, such as breast or ovarian cancer, in particular a cancer with defects in homologous recombinant (HR)-dependent DNA double-strand break (DSB) repair pathway, such as the $brca1^{-/-}$ and/or $brca2^{-/-}$ cancer.

In view of the purpose of improving the therapeutic potential of SOMCL-9112, the present invention seeks to achieve increasing the bioavailability of SOMCL-9112 in a sufficiently high dose formulation. The drug loading of the present invention is up to 60%, but the greater the drug load, the greater the likelihood of instability, and therefore, it is preferable to use a lower drug loading to maintain stability despite a formulation having a drug load of 60%/c can be produced.

As used herein, the term "polymer" refers to a macromolecule consisting of repeating structural units linked by covalent bond. The term includes linear and branched polymers, cyclic polymer such as cyclo-oligosaccharide (including cyclodextrin), homopolymer and copolymer, whether natural, synthetic or semi-synthetic.

As used herein, the term "matrix polymer" refers to a material that exhibits low hygroscopicity and high softening temperature, including polymers or blends of two or more polymers.

As used herein, the term "high softening temperature" means that the glass transition temperature (Tg) or melting point (Tm) of a material measured by differential scanning calorimetry (DSC) is more than 100° C., where Tg is suitable for an amorphous state or form of the polymer, and Tm is suitable for a crystalline state or form of the polymer.

As used herein, the term "surfactant" refers to a pharmaceutically acceptable surfactant. The formulation of the present invention does not comprise or contain more than one surfactant having an HLB value greater than about 4. HLB system is the numerical property of the surfactant, the lipophilic substance obtains a low HLB value, and the hydrophilic substance obtains a high HLB value.

As used herein, the term "solid dispersion" refers to a system in which SOMCL-9112 is dispersed in an excipient carrier. For the drug state in the system, the solid dispersion may in this sense include a composition in which the drug is dispersed in an excipient carrier in a discrete domain of crystalline or non-crystalline drug or in independent molecule. For the entire drug-excipient complex, the solid dispersion may be a relatively large solid material, such as pellet, tablet, film or strip; or they may be present as a free flowing powder consisting of micron or nanoscale primary particles or their aggregates. In the present invention, the definition of the solid dispersion does not include a physical mixture from a dry blending, a wet blending or dry mixing operation and a simple mixture of SOMCL-9112 crystal with other excipients.

As used herein, the term "AUC" refers to the area under the curve of the drug-time, using its conventional meaning, i.e., the area under the plasma concentration-time curve from 0 to 24 hours. AUC has a unit of concentration multiplied by time. Once the test concentration-time point has been determined, the AUC can be easily calculated, for example, by a computer program or by a trapezoidal method.

DETAILED DESCRIPTION OF THE INVENTION

The present invention will now be described in detail with reference to specific examples and data. It should be understood that these examples are merely illustrative and are intended to illustrate the specific formulation, preparation method and function and effect of the invention and are not intended to limit the scope of the invention in any way. In the following examples, the various processes and methods not described in detail are conventional methods known in the art.

In the present invention, the reagents, the sources of the equipment and the trade names used are indicated when their first appeared, and the same reagents used subsequently are the same as those described for the first time unless otherwise stated. The conventional unmarked reagents are purchased from Sinopharm Chemical Reagent Co., Ltd. Among them, the active pharmaceutical ingredient (API) of SOMCL-9112 was synthesized by Shanghai Institute of Materia Medica.

Experiment animals: Both six healthy SD rats, male, weight 200-220 g; and six Beagle dogs, male, weight 10~12 kg come from experiment animal center of Shanghai Institute of Materia Medica. The tested animals were adaptively fed at the test site for 3-7 days before the test day.

Preparation Example

Preparation Example 1

Prescription 1:

| Ingredient | Percentage by weight |
|---|---|
| SOMCL-9112 | 25.0% |
| Copovidone(N-vinylpyrrolidone/vinyl acetate 60:40) | 73.5% |
| Sodium dodecyl sulfate | 0.5% |
| Colloidal silica | 1.0% |

Preparation method: Copovidone (73.5 parts by weight) (N-vinylpyrrolidone/vinyl acetate copolymer, weight ratio 60:40, manufactured by BASF Corporation, VA64), sodium dodecyl sulfate (0.5 parts by weight, manufactured by Anhui sunhere pharmaceutical excipients Co., LTD.) were mixed with SOMCL-9112 (25.0 parts by weight) and colloidal silica (1.0 part by weight, manufactured by Evonik Industries, Ltd., Model: Aerosil), and then the powder mixture was loaded into a double-screw extrude with a extrusion speed of 100 rpm and a temperature of 170° C. (screw diameter: 11 mm; Thermo Scientific Inc). The mixture was extruded in a stripe-like manner by a screw; the hot-melt extruded strip was pulverized and then passed through a 60 mesh sieve to give a SOMCL-9112 solid dispersion.

Figure 1:
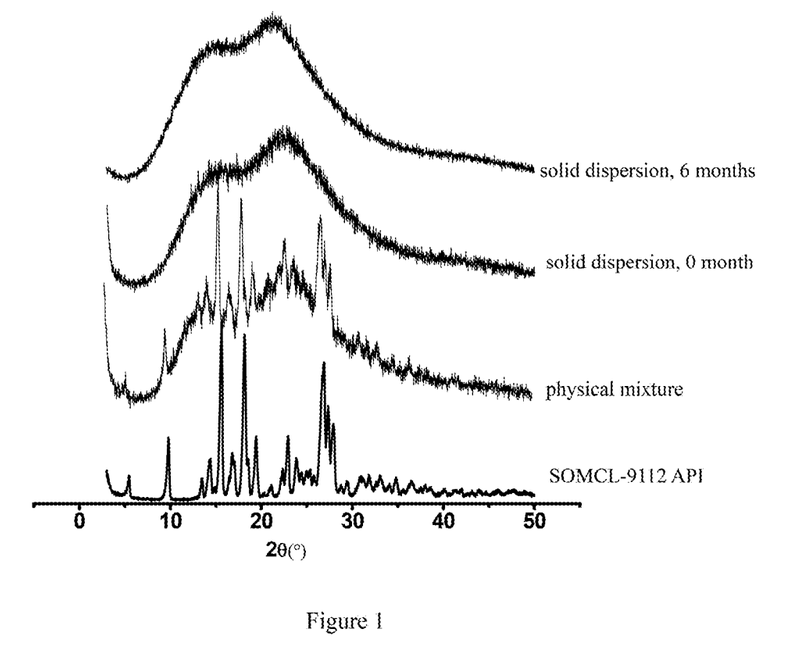
FIG. 1 is an XRPD diffraction pattern of SOMCL-9112 solid dispersion prepared in Preparation Example 1 of the present invention at 0 month and 6 month under accelerated condition.
Figure 2:
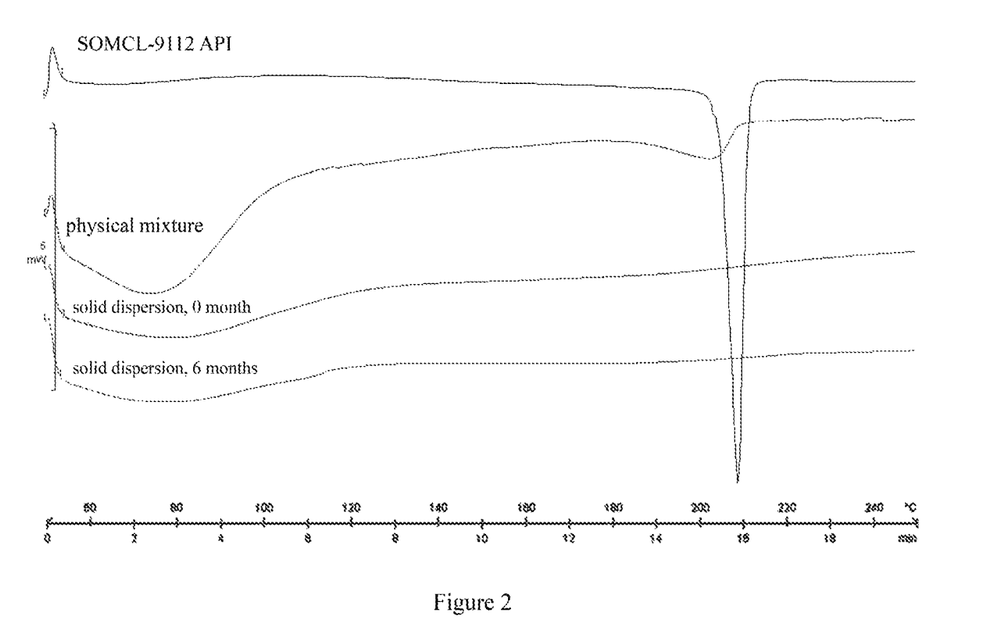
FIG. 2 is a DSC chart of SOMCL-9112 solid dispersion prepared in Preparation Example 1 of the present invention at 0 month and 6 month under accelerated condition.

The X-ray diffraction and differential scanning calorimetry (DSC) of the SOMCL-9112 solid dispersion prepared in this example showed that the drug was dispersed in the amorphous form in the carrier material (0 months). After the SOMCL-9112 solid dispersion was placed under the acceleration condition (40° C.±2° C., 75%±5% RH) for 6 months, the X-ray diffraction and DSC results of the solid dispersion showed that the drug was still dispersed in the amorphous form in the carrier material (FIG. 1, FIG. 2).

Figure 3:
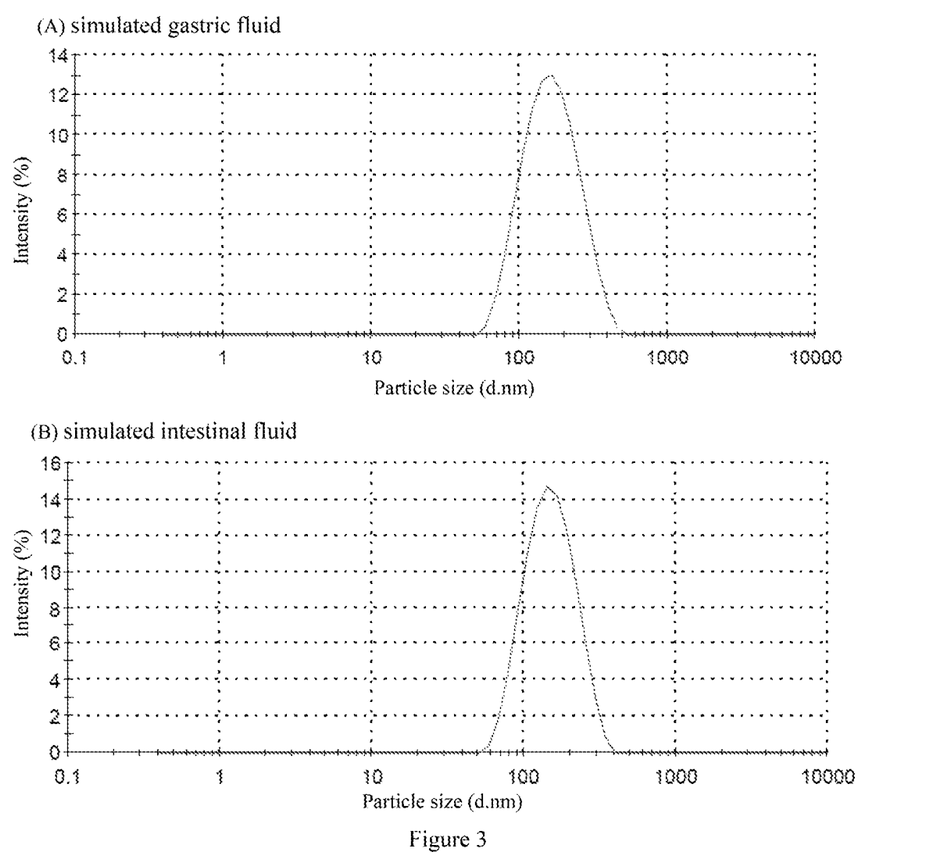
FIG. 3 is a particle size diagram of SOMCL-9112 solid dispersion prepared in Preparation Example 1 of the present invention after diluted in simulated gastric fluid and simulated intestinal fluid, respectively: (A) simulated gastric fluid; (B) simulated intestinal fluid.

The SOMCL-9112 solid dispersion powder prepared in this example was dissolved in simulated gastric fluid (pH 1.2, containing 2 g of KCl and 7 ml of hydrochloric acid per liter) and simulated intestinal fluid (pH6.8, containing 6.8 g of potassium dihydrogen phosphate and 0.944 g sodium hydroxide per liter), respectively, and then the particle size of the formed polymeric micelle was measured (Zetasizer Nano ZS laser particle size analyzer, British Malvern Instruments Co., Ltd.). The measured average particle size of the product was 125.5 nm in the simulated gastric fluid and 116.9 nm in the intestinal fluid (FIG. 3).

The SOMCL-9112 solid dispersion prepared in this Example and the SOMCL-9112 API powder were dissolved in water, simulated gastric fluid (pH 1.2), phosphate buffer (pH 4.5) and simulated intestinal fluid (pH6.8) to measure the solubility of SOMCL-9112 (37° C., shaking at 100 rpm for 8 h). The solid dispersion was sampled at 4 h and 8 h. The results are shown in Table 1. This example showed that the SOMCL-9112 solid dispersion prepared by the present invention can significantly increase the solubility of SOMCL-9112 and that the drug can maintain good solubility at 8 h, which can effectively prevent drug precipitation and ensure effective absorption of the drug in vivo.

TABLE 1

Determination of solubility of SOMCL-9112 APIs and solid dispersions

| Solvent | Solubility (µg/ml) | | |
|---|---|---|---|
| | SOMCL-9112 API | Solid dispersion prepared in Preparation Example 1, 4 h | Solid dispersion prepared in Preparation Example 1, 8 h |
| Water | 15.8 | 456.5 | 451.2 |
| pH 1.2 simulated gastric fluid[1] | 10.5 | 428.3 | 431.7 |
| pH 4.5 phosphate buffer[2] | 18.9 | 318.6 | 314.7 |
| pH 6.8 simulated intestinal fluid[3] | 15.4 | 420.2 | 416.5 |

[1]containing 2 g of KCl and 7 ml of hydrochloric acid per liter
[2]containing 12.9 g of citric acid and 0.63 g of disodium hydrogen phosphate per liter
[3]containing 6.8 g of potassium dihydrogen phosphate and 0.944 g of sodium hydroxide per liter After placed under an acceleration condition (40° C.±2° C., 75%±5% RH) for six months, the solubility of the solid dispersion powder prepared in this example (37° C., shaking at 80 rpm for 8 h) was measured. The solubility was 453.1 µg/ml in water; 430.4 µg/ml in above pH 1.2 simulated gastric fluid, 312.6 µg/ml in above pH 4.5 phosphate buffer and 418.3 µg/ml in above pH 6.8 simulated intestinal fluid, indicating that the solid dispersion of the present invention exhibited a good solubilization effect on SOMCL-9112 after 6 months placement under the accelerated condition.

The solid dispersion prepared in the present example was excellent in stability according to the above-mentioned powder X-ray diffraction, DSC results and solubility measurement results.

Preparation Example 2

Prescription 2:

| Ingredient | Percentage by weight |
|---|---|
| SOMCL-9112 | 25.0% |
| Polyethylene caprolactam-polyvinyl acetate-polyethylene glycol graft copolymer(Soluphlus) | 70.0% |
| Cremophor RH40 | 4.0% |
| Colloidal silica | 1.0% |

Preparation method: Polyethylene caprolactam-polyvinyl acetate-polyethylene glycol graft copolymer (70.0 parts by weight) (Soluplus, manufactured by BASF Corporation, Germany), Cremerphor RH40 (4.0 parts by weight) (manufactured by BASF Corporation, Germany) and SOMCL (95.0 parts by weight) and colloidal silica (1.0 part by weight) were mixed, and the powdery mixture was charged into a twin screw extruder (screw diameter: 11 mm) having an extrusion speed of 150 rpm and a temperature of 160° C. The mixture was extruded in a stripe-like manner by a screw; the hot-melt extruded strip was pulverized and then passed through a 60 mesh sieve to give a SOMCL-9112 solid dispersion.

The SOMCL-9112 solid dispersion prepared in this example was dissolved in water, simulated gastric fluid (pH 1.2), phosphate buffer (pH 4.5) and simulated intestinal fluid (pH6.8) to measure the solubility of SOMCL-9112 (37° C., shaking at 100 rpm for 8 h). The measured solubility of the SOMCL-9112 solid dispersion was 421.7 µg/ml in water; 411.4 µg/ml in pH 1.2 simulated gastric fluid, 308.5 µg/ml in pH 4.5 phosphate buffer and 403.1 µg/ml in pH 6.8 simulated intestinal fluid. The example showed that the prepared SOMCL-9112 solid dispersion can significantly increase the solubility of SOMCL-9112.

Preparation Example 3

Prescription 3:

| Ingredient | Percentage by weight |
|---|---|
| SOMCL-9112 | 30.0% |
| Hydroxypropylmethylcellulose acetate succinate(HPMCAS) | 64.0% |
| Sodium dodecyl sulfate | 2.0% |
| Triethyl citrate | 3.0% |
| Colloidal silica | 1.0% |

Preparation method: Hydroxypropylmethylcellulose acetate succinate (64.0 parts by weight) (HPMCAS, manufactured by Shin-Etsu Chemical Co., Ltd., Japan), sodium dodecyl sulfate (2.0 parts by weight) (manufactured by BASF Corporation, Germany), and triethyl citrate (3.0 parts by weight) (Anhui Fengyuan Pharmaceutical Co., Ltd.) were mixed with SOMCL-9112 (30.0 parts by weight) and colloidal silica (1.0 part by weight), and the powdery mixture was charged into a twin screw extruder (screw diameter: 11 mm) having an extrusion speed of 100 rpm and a temperature of 140° C. The mixture was extruded in a stripe-like manner by a screw; the hot-melt extruded strip was pulverized and then passed through a 60 mesh sieve to give a SOMCL-9112 solid dispersion.

The SOMCL-9112 solid dispersion prepared in this example was dissolved in a simulated intestinal fluid (pH6.8) to measure the solubility of SOMCL-9112 (37° C., shaking at 100 rpm for 8 h). The measured solubility of the SOMCL-9112 solid dispersion in pH 6.8 simulated intestinal fluid was 379.4 µg/ml. The example showed that the prepared SOMCL-9112 solid dispersion can significantly increase the solubility of SOMCL-9112.

Preparation Example 4

Prescription 4:

| Ingredient | Percentage by weight |
|---|---|
| SOMCL-9112 | 30.0% |
| Copovidone(N-vinylpyrrolidone/vinyl acetate60:40) | 70.0% |

Preparation method: Copovidone (N-vinylpyrrolidone/vinyl acetate copolymer, 60:40 by weight) (70.0 parts by weight) and SOMCL-9112 (30.0 parts by weight) were dissolved in a mixed solvent of acetone/ethanol (4:1 by volume) and the solvent was then allowed to dry at 30° C. by means of a rotary evaporator. The resulting material was dried in a vacuum oven at 40° C. for more than 12 h to remove the residual organic solvent. The resulting solid material was pulverized and then passed through 60 mesh sieve to give a SOMCL-9112 solid dispersion.

The SOMCL-9112 solid dispersion prepared in this example was dissolved in water, simulated gastric fluid (pH 1.2), phosphate buffer (pH 4.5) and simulated intestinal fluid (pH6.8) to measure the solubility of SOMCL-9112 (37° C., shaking at 100 rpm for 8 h). The measured solubility of the SOMCL-9112 solid dispersion was 463.5 µg/ml in water, 425.7 µg/ml in pH 1.2 simulated gastric fluid, 321.6 µg/ml in pH4.5 phosphate buffer and 422.6 µg/ml in pH 6.8 simulated intestinal fluid. The example showed that the prepared SOMCL-9112 solid dispersion can significantly increase the solubility of SOMCL-9112.

Preparation Example 5

The SOMCL-9112 solid dispersion (80.0 parts by weight) obtained in Preparation Example 1 was mixed uniformly with mannitol (14.2 parts by weight) (manufactured by French Roger Company), crospovidone (4.8 parts by weight) (PVPP, manufactured by International Specialty Chemicals Co., Ltd., US) and sodium stearyl fumarate (1.0 part by weight) (manufactured by JRS Group Pharmaceuticals Co., Ltd., Germany) and compressed into 500.0 mg tablets using a single punch tablet machine. The tablets were then placed in a coating pan and coated with a film by using a water-based dispersion liquid for film coating (Opadry, manufactured by Shanghai Colorcon Coating Technology Co., Ltd.) at a temperature of 60° C.

Preparation Example 6

The SOMCL-9112 solid dispersion (80.0 parts by weight) obtained in Preparation Example 2 was mixed uniformly with microcrystalline cellulose (13.8 parts by weight) (manufactured by Taiwan Mingtai Chemical Industry Co., Ltd.), sodium dodecyl sulfate (1.2 parts by weight), cross-linked carboxymethylcellulose sodium (4.0 parts by weight) (manufactured by JRS Group Pharmaceuticals Co., Ltd., Germany) and magnesium stearate (1.0 part by weight) (manufactured by Anhui Shanhe Pharmaceutical Co., Ltd.) and compressed into 250.0 mg tablets. The tablets were then placed in a coating pan and coated with a film by using a water-based dispersion liquid for film coating (Opadry, manufactured by Shanghai Colorcon Coating Technology Co., Ltd.) at a temperature of 60° C.

Preparation Example 7

The SOMCL-9112 solid dispersion (66.7 parts by weight) obtained in Preparation Example 3 was mixed uniformly with lactose (26.3 parts by weight) (manufactured by DFE Pharma Co., Ltd., Netherlands), crospovidone (6.0 parts by weight) and magnesium stearate (1.0 parts by weight) and filled into capsules at 250 mg/capsule (1 #) using a capsule filling machine

Comparative Example

Comparative Example 1

The SOMCL-9112 API (20.0 parts by weight), polyethylenecaprolactam-polyvinyl acetate-polyethylene glycol graft copolymer (Soluplus, 56.0 parts by weight), microcrystalline cellulose (13.8 parts by weight), sodium dodecyl sulfate (2.4 parts by weight), colloidal silica (0.8 parts by weight), crospovidone (6.0 parts by weight) and magnesium stearate (1.0 part by weight) were uniformly mixed and compressed into conventional IR tablets (250.0 mg each) using a single punch tablet machine. The tablets were then placed in a coating pan and coated with a film by using a water-based dispersion liquid for film coating (Opadry, manufactured by Shanghai Colorcon Coating Technology Co., Ltd.) at a temperature of 60° C.

Comparative Example 2

The SOMCL-9112 API (0.5 parts by weight) was dispersed in 0.2% poloxamer 407 (99.5 parts by weight) (manufactured by BASF Corporation, Germany) solution under high-shear for 3 min and then homogenized using a micro-jet homogenizer Nano DB at a pressure of 20000 PSI for 10 min (gap D8) to obtain a nano-crystal suspension having an average particle size of 359 nm.

Comparative Example 3

The SOMCL-9112 API (1.0 parts by weight), propanediol (25.0 parts by weight) (manufactured by Dow Chemical Company, US), MCT (15.0 parts by weight) (manufactured by Tieling North Asia Pharmaceutical Co., Ltd.) and Solutol HS 5 (59.0 parts by weight) were placed into a suitable container and stirred at 300 rpm at 50-70° C. until SOMCL-9112 was completely dissolved to obtain a SOMCL-9112 liquid preparation containing SOMCL-9112 at a concentration of 10 mg/ml (1% by weight).

Experiment Example

Experiment Example 1

Study on Equilibrium Solubility and Permeability

Equilibrium Solubility Test: The solubility of SOMCL9112 in a series of solvents was investigated. The main solvents included water, pH 1.2 simulated gastric fluid, pH 4.5 phosphate buffer, and pH 6.8 simulated intestinal fluid. 0.5 g of SOMCL-9112 API was taken and added to 100 ml of each of the above solvents. The mixture was shaken at 37° C. shaker at 100 rpm for 24 h. The supernatant was centrifuged at 8000 rpm for 15 min and the concentration of SOMCL-9112 was determined by HPLC. The solubility of SOMCL-9112 in different media was shown in Table 2.

TABLE 2

Solubility of SOMCL-9112 in different solvents

| Solvent | Equilibrium Solubility (μg/ml), 24 h |
|---|---|
| Water | 14.8 |
| pH 1.2 simulated gastric fluid | 10.3 |
| pH 4.5 phosphate buffer | 18.6 |
| pH 6.8 simulated intestinal fluid | 16.2 |

Permeability Test: The permeability of SOMCL-9112 was evaluated using Caco-2 cell model. Concentrations of SOMCL-9112, positive control atenolol, propranolol and digoxin were determined by LC/MS/MS. The ratio of apparent permeability coefficient (Papp) to apparent permeability coefficient (Papp ratio=$Papp_{(B \to A)}/Papp_{(A \to B)}$ was calculated to determine the permeability of the compound and whether it is a substrate of P-gp. The results were shown in Table 3.

TABLE 3

SOMCL-9112 permeability in Caco-2 cell model (n = 3, ±SD)

| Compound | Papp($10^{-6}$ cm/s) | | Papp ratio |
|---|---|---|---|
| | A→B | B→A | |
| Atenolol | 0.92 ± 0.15 | 1.16 ± 0.17 | 1.26 |
| Propranolol | 10.5 ± 1.97 | 7.57 ± 0.60 | 0.72 |
| Digoxin | 0.09 ± 0.01 | 9.88 ± 1.41 | 109.0 |
| SOMCL-9112(2.00 μM) | 0.72 ± 0.036 | 16.3 ± 0.34 | 22.6 |
| SOMCL-9112(10.0 μM) | 0.26 ± 0.03 | 16.1 ± 1.05 | 61.9 |
| SOMCL-9112(50.0 μM) | 0.34 ± 0.06 | 18.7 ± 0.28 | 54.5 |

Note:
A = top, B = outside of the base
The above results indicate that SOMCL-9112 has a low permeability characteristic and has a significant efflux effect on Caco-2 cells in the range of 2.00-50.0 μM.

Experiment Example 2

In Vitro Dissolution Test

The dissolution rate of the preparations prepared in Preparation Example 5, Preparation Example 6 and Preparation Example 7 and Comparative Example 1 was measured according to the second method (paddle method) of the Chinese Pharmacopoeia 2010 edition II Appendix XC. A single dosage unit of formulation was placed in a simulated intestinal fluid (900 ml, pH6.8) at 37° C. and stirred at 75 rpm. After 15, 30, 60, 90 and 120 min, 8 ml of the sample was taken and the same volume of fluid was given. The sample was diluted for 4 times and the absorbance was measured at the wavelength of 240 nm by UV-Vis spectrophotometry (Chinese Pharmacopoeia 2010 edition II Appendix IVA). The dissolution quantity of the corresponding preparation was calculated and the dissolution profile was plotted (see FIG. 4).

Figure 5:
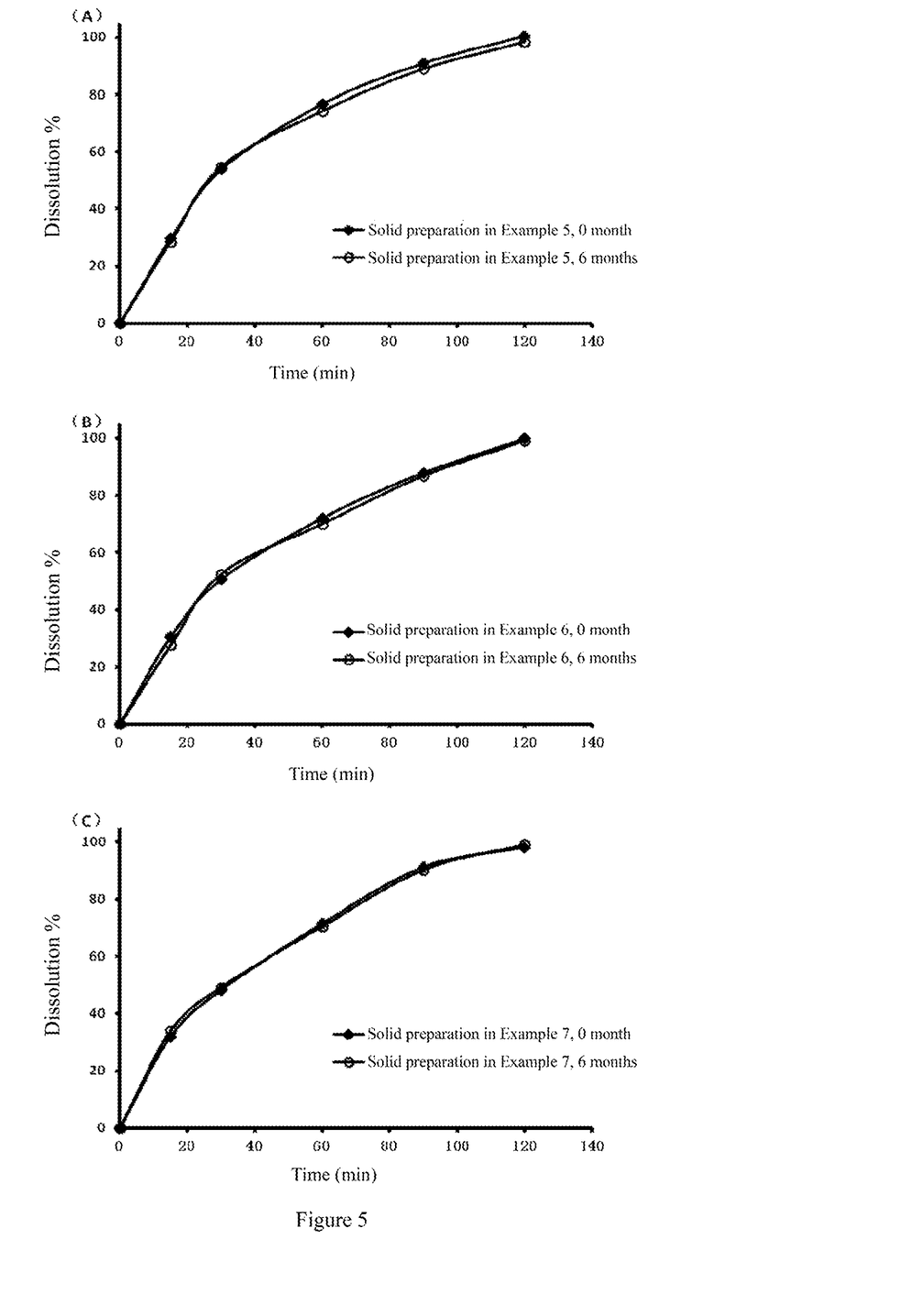
FIG. 5 compares in vitro dissolution curves of various SOMCL-9112 formulations prepared in Preparation Examples 5, 6, and 7 at 0 month and 6 month under accelerated condition (n=6).

The SOMCL-9112 solid preparations prepared in Preparation Example 5, 6 and 7 of the present invention were placed under an acceleration condition (40±2° C., 75%±5% RH) for 6 months, then the dissolution behavior of the drug was measured using the same conditions and the dissolution profile was plotted (see FIG. 5).

Figure 4:
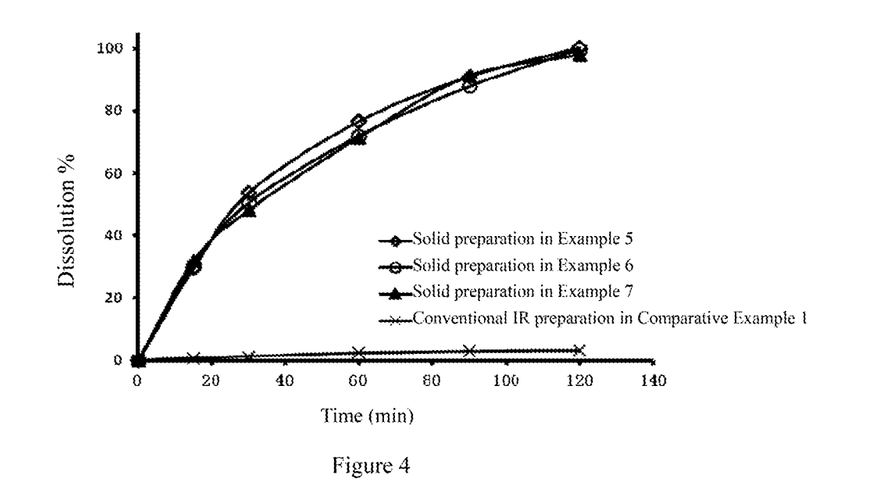
FIG. 4 is an in vitro dissolution curve of various SOMCL-9112 formulations prepared in Preparation Examples 5, 6, and 7 and Comparative Example 1 of the present invention (n=6).

It can be seen from the results that the SOMCL-9112 solid preparation prepared in Examples 5, 6 and 7 of the present invention can significantly improve the dissolution rate and solubility of SOMCL-9112 compared with the conventional IR formulation. After placed under an acceleration condition, there is no significant change in the dissolution behavior of the formulation of the present invention. The drug solubilization effect is good and the stability is good.

Experiment Example 3

Study on Relative Bioavailability

The preparations prepared in Preparation Example 1 and Comparative Example 2 were intragastrically administered to the fasting SD rats (experiment animal center of Shanghai Institute of Materia Medica) (n=3). The sample prepared in Preparation Example 1 was prepared into a SOMCL-9112 solution (2 mg/ml) by using purified water and then administered. The administration dosage of each preparation was 20 mg/kg. The rats were fasted with free access to water for 12 h before test and taken food at 2 h after administration. 0.3 ml of venous blood was taken from the venous plexus of the rat before administration (0 h) and at 0.25, 0.5, 1.0, 2.0, 3.0, 4.0, 6.0, 8.0 and 24 hours after administration, placed into a heparinized test tube and centrifuged at 11000 rpm for 5 min to separate plasma. The samples were stored in a −20° C. refrigerator until test.

The above-mentioned Comparative Example 2 preparation (containing 2 mg/ml of SOMCL-9112) was taken and administered to fasting SD rats (experiment animal center of Shanghai Institute of Materia Medica) (n=3) through intravenous injection at a dose of 10 mg/kg. Before administration (0 h) and 5 min, 0.25, 0.5, 1.0, 2.0, 4.0, 6.0, 8.0 and 24 hours after administration, 0.3 ml venous blood was taken from the venous plexus of the rat was taken, placed into a heparinized test tube and centrifuged at 11000 rpm for 5 min to separate plasma. The samples were stored in a −20° C. refrigerator until test.

The concentration of SOMCL-9112 in the sample was determined by LC-MS. The pharmacokinetic parameters of SOMCL-9112 after administered to SD rats were calculated using the non-compartmental model of Phoenix 1.3 software (Pharsight, USA). The data are summarized in Table 4.

TABLE 4

Summary of in vivo pharmacokinetic data of SOMCL-9112 in SD rats (n = 3)

| Preparation | $T_{1/2}$ (h) | Cmax (ng/ml) | $AUC_{(0-t)}$ (h * ng/ml) | Relative bioavailability (F, %) |
|---|---|---|---|---|
| Preparation Example 1 | 4.73 | 1247.0 | 913 | 724.6 |
| Comparative Example 1 | 7.69 | 14.0 | 126 | / |

As a result, it can be seen that the preparation prepared by the present invention can significantly increase the exposure amount of SOMCL-9112 in SD rats compared with nanocrystal preparation of SOMCL-9112 thereby significantly increasing the relative bioavailability of SOMCL-9112.

Experiment Example 4

Study on Absolute Bioavailability

The preparation prepared in the above Preparation Example 5 was orally administered to fasting Beagle Dogs (experiment animal center of Shanghai Institute of Materia Medica) (n=3) at a dose of 100 mg/dog. The dogs were fasted with free access to water for 12 h before test and given with food at 4 h after administration. These preparations were delivered with 30 ml of water. 0.8 ml blood sample was taken before administration (0 h) and at 0.25, 0.5, 1.0, 2.0, 3.0, 4.0, 6.0, 8.0, 12 and 24 hours after administration, placed into a heparinized test tube and centrifuged at 3500 rpm for 10 min to separate plasma. The samples were stored in a −70° C. refrigerator until test.

The preparation of the above Comparative Example 3 was diluted for 8 times with physiological saline and administered intravenously to the fasting dogs (n=3) at a dose of 5 mg/kg (2 ml/kg) of SOMCL-9112. Before administration (0 h) and 5 min, 0.25, 0.5, 1.0, 2.0, 3.0, 4.0, 6.0, 8.0, 12 and 24 hours after administration, 0.8 ml blood sample was taken, placed into a heparinized test tube and centrifuged at 3500 rpm for 10 min to separate plasma. The samples were stored in a −70° C. refrigerator until test.

The concentration of SOMCL-9112 in the sample was determined by LC-MS. The pharmacokinetic parameters of SOMCL-9112 after administered to Beagle Dog were calculated using the non-compartmental model of Phoenix 1.3 software (Pharsight, USA). The data are summarized in Table 5.

TABLE 5

Summary of Pharmacokinetic Data for SOMCL-9112 (n = 3)

| Preparation | $T_{1/2}$ (h) | Cmax (ng/ml) | $AUC_{(0-\infty)}$ (h * ng/ml) | Absolute bioavailability (%) |
|---|---|---|---|---|
| Preparation Example 5 | 2.60 | 4723 | 22507 | 40.2 |
| Intravenous preparation | 2.71 | / | 22763 | / |

It can be seen from the results that the SOMCL-9112 solid preparation of the present invention significantly improves the bioavailability of SOMCL-9112 and is well absorbed in vivo.

The invention claimed is:

1. A SOMCL-9112 solid dispersion, wherein it comprises the following raw materials and is prepared based on the weight percentages,

| | |
|---|---|
| SOMCL-9112 | 5%-60%, |
| a pharmaceutically acceptable matrix polymer | 5%-90%, |
| a surfactant | 0%-20%, |
| a glidant | 0%-20%, and |
| a plasticizer | 0%-20%, | wherein the pharmaceutically acceptable matrix polymer is copovidone or polyvinyl caprolactam-polyvinyl acetate-polyethylene glycol graft copolymer.

2. The SOMCL-9112 solid dispersion of claim 1, wherein the proportion of SOMCL-9112 present in an amorphous form in SOMCL-9112 ranges from 70% to 100%.

3. The SOMCL-9112 solid dispersion of claim 1, wherein the surfactant is one or more selected from a group consisting of anionic surfactant, cationic surfactant and nonionic surfactant; and/or
the glidant is one or more selected from a group consisting of colloidal silica, animal or vegetable fat, wax; and/or
the plasticizer is one or more selected from a group consisting of acetyl tributyl citrate, acetyl triethyl citrate, benzyl benzoate, chlorobutanol, dextrin, dibutyl phthalate, diethyl phthalate, dimethyl phthalate, glycerol, glyceryl monostearate, mannitol, mineral oil, lanolin alcohol, palmitic acid, polyethylene glycol, polyvinyl acetate phthalate, propylene glycol, 2-pyrrolidone, sorbitol, stearic acid, triacetin, tributyl citrate, triethanolamine and triethyl citrate.

4. The SOMCL-9112 solid dispersion of claim 1, wherein the weight ratio of SOMCL-9112 to the pharmaceutically acceptable matrix polymer is from 1:0.25 to 1:10.

5. A preparation method for the SOMCL-9112 solid dispersion of claim 1, wherein, it comprises the following steps:
(1) uniformly mixing raw materials by melting or dissolving to obtain a homogeneous dispersion;
(2) solidifying the homogeneous dispersion to give SOMCL-9112 solid dispersion wherein SOMCL-9112 is present in an amorphous form.

6. The preparation method of claim 5, wherein it comprises the following steps:
(1a) mixing the raw materials and heating to produce a melt;
(2a) extruding the melt to cure for producing a SOMCL-9112 solid dispersion, wherein the heating temperature in step (1a) is 70° C. 250° C., 80° C.-200° C., or 100° C.-180° C.

7. The preparation method of claim 5, wherein it comprises the following steps:
(1b) dissolving the raw materials in a solvent;
(2b) evaporating the solvent to produce a SOMCL-9112 solid dispersion wherein SOMCL-9112 is present in an amorphous form,
wherein the solvent in step (1b) is acetone, acetone/dichloromethane, methanol/dichloromethane, acetone/water, acetone/methanol, acetone/ethanol, dichloromethane/ethanol or ethanol/water.

8. A SOMCL-9112 solid preparation, wherein it comprises the SOMCL-9112 solid dispersion of claim 1 and at least one non-essential pharmaceutical additive selected from the group consisting of a disintegrant, a filler, a lubricant, and a coating agent.

9. The SOMCL-9112 solid preparation of claim 8, wherein the SOMCL-9112 solid preparation is tablet, capsule, granule, or powder.

10. A method for treating cancer comprising the step of administering the SOMCL-9112 solid dispersion of claim 1 to a subject in need thereof, wherein the cancer is breast cancer, ovarian cancer, or pancreatic cancer.

11. The SOMCL-9112 solid dispersion of claim 3, wherein
the surfactant is one or more selected from a group consisting of one or more of sodium dodecyl sulfate, docusate sodium, bromo-trimethylammonium, benzethonium chloride, cetylpyridinium chloride, lauric acid polyoxyethylene alkyl ether, polyoxyethylene sorbitan fatty acid ester, polyoxyethylene castor oil derivative, polyoxyethylene stearate and poloxamer.

12. The SOMCL-9112 solid dispersion of claim 11, wherein the surfactant is sodium dodecyl sulfate.

13. The SOMCL-9112 solid dispersion of claim 4, wherein the weight ratio of SOMCL-9112 to the pharmaceutically acceptable matrix polymer is from 1:0.3 to 1:7.

14. The SOMCL-9112 solid dispersion of claim 4, wherein the weight ratio of SOMCL-9112 to the pharmaceutically acceptable matrix polymer is from 1:0.5 to 1:5.

15. The SOMCL-9112 solid dispersion of claim 4, wherein the weight ratio of SOMCL-9112 to the pharmaceutically acceptable matrix polymer is from 1:2 to 1:4.

16. A SOMCL-9112 solid dispersion, wherein it comprises the following raw materials and is prepared based on the weight percentages,

| | |
|---|---|
| SOMCL-9112 | 10%-50%, |
| a pharmaceutically acceptable matrix polymer | 10%-80%, |
| a surfactant | 0.5%-15%, |
| a glidant | 0%-15%, and |
| a plasticizer | 0%-10%, | wherein the pharmaceutically acceptable matrix polymer is copovidone or polyvinyl caprolactam-polyvinyl acetate-polyethylene glycol graft copolymer.

17. The SOMCL-9112 solid dispersion of claim 16, wherein the proportion of SOMCL-9112 present in an amorphous form in SOMCL-9112 ranges from 70% to 100%.

18. The SOMCL-9112 solid dispersion of claim 16, wherein
the surfactant is one or more selected from a group consisting of one or more of sodium dodecyl sulfate, docusate sodium, bromo-trimethylammonium, benzethonium chloride, cetylpyridinium chloride, lauric acid polyoxyethylene alkyl ether, polyoxyethylene sorbitan fatty acid ester, polyoxyethylene castor oil derivative, polyoxyethylene stearate and poloxamer; and/or
the glidant is one or more selected from a group consisting of colloidal silica, animal or vegetable fat, wax; and/or
the plasticizer is one or more selected from a group consisting of acetyl tributyl citrate, acetyl triethyl citrate, benzyl benzoate, chlorobutanol, dextrin, dibutyl phthalate, diethyl phthalate, dimethyl phthalate, glycerol, glyceryl monostearate, mannitol, mineral oil, lanolin alcohol, palmitic acid, polyethylene glycol, polyvinyl acetate phthalate, propylene glycol, 2-pyrrolidone, sorbitol, stearic acid, triacetin, tributyl citrate, triethanolamine and triethyl citrate.

19. The SOMCL-9112 solid dispersion of claim 16, wherein the weight ratio of SOMCL-9112 to the pharmaceutically acceptable matrix polymer is from 1:0.25 to 1:10.

20. The SOMCL-9112 solid dispersion of claim 18, wherein the surfactant is sodium dodecyl sulfate.

21. A SOMCL-9112 solid dispersion, wherein it comprises the following raw materials and is prepared based on the weight percentages,

| | |
|---|---|
| SOMCL-9112 | 5%-60%, |
| a pharmaceutically acceptable matrix polymer | 5%-90%, |
| a surfactant | 0%-20%, |
| a glidant | 0%-20%, and |
| a plasticizer | 0%-20%, | wherein the pharmaceutically acceptable matrix polymer is copovidone or polyvinyl caprolactam-polyvinyl acetate-polyethylene glycol graft copolymer;
the surfactant is sodium dodecyl sulfate;
the glidant is colloidal silica; and
the plasticizer is mannitol.

22. The SOMCL-9112 solid dispersion of claim 21, wherein it comprises the following raw materials and is prepared based on the weight percentages,

| | |
|---|---|
| SOMCL-9112 | 10%-50%, |
| a pharmaceutically acceptable matrix polymer | 10%-80%, |
| a surfactant | 0.5%-15%, |
| a glidant | 0%-15%, and |
| a plasticizer | 0%-10%, | wherein the pharmaceutically acceptable matrix polymer is copovidone;
the surfactant is sodium dodecyl sulfate;
the glidant is colloidal silica; and
the plasticizer is mannitol.

23. The SOMCL-9112 solid dispersion of claim 21, wherein the weight ratio of SOMCL-9112 to copovidone is from 1:2 to 1:4.

24. The SOMCL-9112 solid dispersion of claim 21, wherein it comprises the following raw materials and is prepared based on the weight percentages,

| | |
|---|---|
| SOMCL-9112 | 25%, |
| copovidone | 73.5%, |
| sodium dodecyl sulfate | 0.5%, and |
| colloidal silica | 1%. |

25. The SOMCL-9112 solid dispersion of claim 21, wherein it comprises the following raw materials and is prepared based on the weight percentages,

| | |
|---|---|
| SOMCL-9112 | 20%-25%, |
| copovidone | 70%-73.5%, |
| sodium dodecyl sulfate | 2.4%, and |
| colloidal silica | 1%. |

26. A SOMCL-9112 solid preparation, wherein it comprises the SOMCL-9112 solid dispersion of claim 21 and at least one non-essential pharmaceutical additive selected from the group consisting of a disintegrant, a filler, a lubricant, and a coating agent.

27. The SOMCL-9112 solid preparation of claim 26,
wherein the at least one non-essential pharmaceutical additive is the lubricant or the disintegrant,
wherein the lubricant is sodium stearyl fumarate, and
wherein the disintegrant is cross-linked polyvinylpyrrolidone.

28. The SOMCL-9112 solid preparation of claim 26, wherein the SOMCL-9112 solid preparation is tablet, capsule, granule, or powder.

* * * * *